United States Patent [19]

Tennant

[11] 4,254,510
[45] Mar. 10, 1981

[54] IMPLANT LENS WITH BIARCUATE FIXATION

[76] Inventor: Jerald L. Tennant, 806 Greentree Ct., Duncanville, Tex. 75137

[21] Appl. No.: 49,551

[22] Filed: Jun. 18, 1979

[51] Int. Cl.³ ............................ A61F 1/16; A61F 1/24
[52] U.S. Cl. ........................................................... 3/13
[58] Field of Search ......................................... 3/13, 1

[56] References Cited

U.S. PATENT DOCUMENTS

| | | | |
|---|---|---|---|
| 2,834,023 | 5/1958 | Lieb | 3/13 X |
| 3,961,379 | 6/1976 | Highgate | 3/13 |
| 3,992,563 | 11/1976 | Tanaka | 3/13 |
| 4,092,743 | 6/1978 | Kelman | 3/13 |
| 4,174,543 | 11/1979 | Kelman | 3/13 |

OTHER PUBLICATIONS

"Experience with Twelve Cases of Intra-Ocular Anterior Chamber Implants for Aphakia," by J. Boberg-Ans, British Journal of Ophthalmology, vol. 45, No. 1, Jan. 1961, pp. 37–43.
"The Intraocular Implant Lens Development and Results with Special Reference to the Binkhorst Lens," by M. E. Nordlohne (Book), Second Edition, The Williams and Wilkins Company, Baltimore, pp. 14–20, 1975 (p. 16, Shreck Lens).

*Primary Examiner*—Ronald L. Frinks

[57] ABSTRACT

An intraocular implant unit having a lens (10) with a first limb (11) and a second limb (12) integral therewith and extending outward radially from opposite margins thereof. A long arcuate rim (13) is centered on the end of the first limb (11) and a short arcuate rim (14) is centered on said second limb (12) wherein the rims (13, 14) and limbs (11, 12) are substantially less in lateral dimension than the diameter of the lens (10) for minimizing the weight of the implant unit while assuring positive fixation.

12 Claims, 5 Drawing Figures

IMPLANT LENS WITH BIARCUATE FIXATION

TECHNICAL FIELD

This invention relates to intraocular implant lenses and more particularly to a lens of light weight wherein the implanted weight is distributed over a large area to minimize the localization of support forces.

BACKGROUND ART

Lens implants on patients requiring surgery because of the presence of cataracts are widely practiced. Developments leading to acceptance of the technique and of lenses designed for implant are discussed in "A Lens For All Seasons" by Jerald L. Tennant, 1976. The development of the Choyce lens and the Tennant lens has lead to wide acceptance with many hundreds of implants being performed using such lenses. In such systems the lens is placed in the anterior chamber. Fixation of the lens is assured by four point contacts made by feet extending from the lens proper.

It has been found to be desirable to minimize the localization of the lens contact with the supporting tissues. Localized pressure by some prior art lenses has a tendency to cause distortion of the pupil after a period of time. Thus, the present invention is directed towards a lens suitable for implant in either the anterior chamber or the posterior chamber with minimal tissue loading.

DISCLOSURE OF THE INVENTION

In accordance with the present invention an intraocular implant lens unit is provided comprising a central lens structure having a narrow twelve o'clock limb and a narrow six o'clock limb integral with and extending radially from opposite margins of the lens. A narrow arcuate rim segment is centered on and is integral with the end of the twelve o'clock limb and extends for about the width of the optic. A narrow arcuate rim segment is centered on and is integral with the end of the six o'clock limb and extends for about twice the width of the optic. The arcs have a center at the center of the lens and are of diameter corresponding to the diameter of the chamber in which it is to be fitted so that the outer edges of the rim segments bear against the inner wall of the chamber.

DETAILED DESCRIPTION OF THE DRAWINGS

Figure 1:
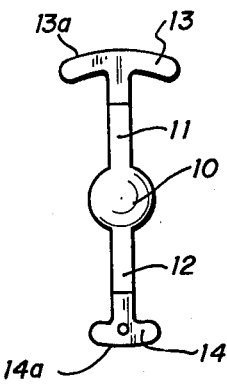
Figure 2:
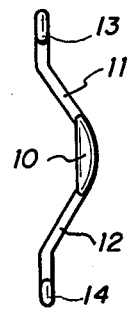
Figure 3:
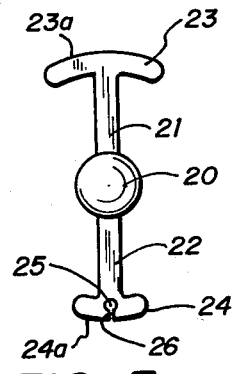
Figure 4:
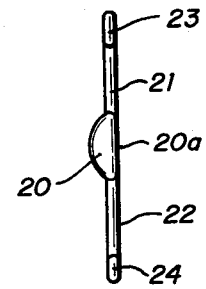
Figure 5:
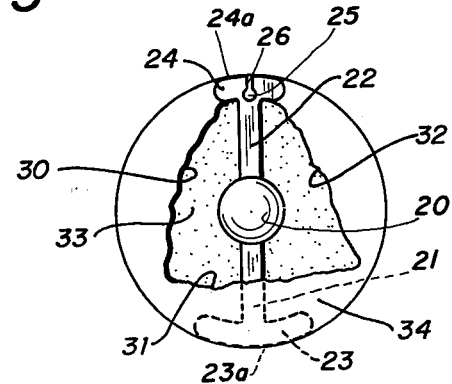

FIG. 1 is a front view of an anterior chamber lens;
FIG. 2 is a side view of the lens of FIG. 1;
FIG. 3 is a front view of a posterior chamber lens;
FIG. 4 is a side view of the lens of FIG. 3; and
FIG. 5 illustrates the lens of FIGS. 3 and 4 mounted within the posterior capsule.

DETAILED DESCRIPTION

FIGURE 1

Referring to FIG. 1 an optic lens 10 of plano-convex shape is formed integrally with a six o'clock limb 11 and a twelve o'clock limb 12. Limbs 11 and 12 thus extend diametrically in opposite directions from the lens 10. A rim segment 13 is integral with and formed at the end of the limb 11 opposite lens 10. The arc segment 13 spans an arc of about 60° and is of generally the same thickness and width as the limb 11. It lies in the plane perpendicular to the axis of the lens 10 and presents a curved outer surface 13a which is preferably rounded on the edges and smooth to provide contact over the entire length of the surface 13a with the margin of the anterior chamber into which the lens is to be placed.

A second rim segment 14 is integrally formed with and is located at the end of the twelve o'clock limb 12. The rim segment 14 preferably is of a chord length equal to the diameter of the lens 10. It is much shorter than the rim segment 13 and is designed to engage along its outer surface 14a and the inner margin of the anterior chamber in which it is to be located.

In a typical embodiment, the lens 10 would have a diameter of 4 to 6 millimeters; thus, the chord length of the rim segment 14 would be 4 to 6 millimeters. The chord length of the rim segment 13 would be approximately twice the chord length of the rim segment 14, i.e., 8 to 12 millimeters. Typically the radius of the outer surfaceS 13a and 14a of rim segments 13 and 14 would be of the order of 12.5 millimeters.

FIGURE 2

FIG. 2 is a side view of an embodiment of FIG. 1 wherein the lens 10 is plano-convex. It will be noted that the limbs 11 and 12 extend posteriorly relative to the posterior surface of lens 10 as well as radially.

It is to be noted that the implant unit of FIGS. 1 and 2 essentially retain the equivalent of four point fixation which prevents rotation of the lens. Rotation is also discouraged by having the long inferior rim. The inability to rotate is an important feature.

Corneal dystrophies of older triangular lenses such as known in the prior art occur primarily when the lens rotates in the eye causing continual endothelial cell damage. The weight of lenses currently used in greatest volume cannot be reduced by simply fenestrating the lens. Such expedients have been tried and found that the iris would herniate through the fenestrations. Further where point contact is made between a foot of a lens and the iris, there is a tendency to incarcerate the lens in the iris or in the ciliary body. Such incarceration is avoided with the lens shown in FIGS. 1 and 2 since the rim surfaces 13a and 14a have the same radius as the radius of the scleral spur.

By providing the limbs 11 and 12 with posterior inclination as well as radial extension, clearance of the iris of from ½ to ¾ of a millimeter is provided to avoid rubbing of the iris tissue.

While the optic of FIGS. 1 and 2 has been shown as of plano-convex configuration it will be understood that it may be made convex-plano or biconvex. However, plano-convex configuration is preferred inasmuch as it provides maximum spacing between the iris and the posterior surface of the lens. Irritation in the postoperative period of the raw edges of the iris is thus avoided.

FIGURE 3

FIG. 3 illustrates a lens embodying the present invention suitable to be placed in the posterior chamber of an eye after an extra-capsular cataract extraction has been performed. It is not suitable, of course, for use after intracapsular extraction inasmuch as the capsule itself is used for fixation.

Referring to FIG. 3, lens 20 is provided with radial limbs 21 and 22. Limb 21 is integral at the end thereof with a rim segment 23 and has generally the same characteristics as above described in connection with FIG. 1.

Similarly limb 22 terminates in and is integral with a shorter rim segment 24. Rim segment 24 is pierced by a small hole 25 which is centered on a radius extending from the center of lens 20 and is centered in the rim segment 24. A slit 26 extends from the aperture 25 about to the surface 24a of the rim segment 24.

FIGURE 4

As shown in FIG. 4 lens 20 is plano-convex and has an anterior surface 20a which lies in the same plane as the anterior surface of the limbs 21 and 22 and the anterior surface of the rim segments 23 and 24.

FIGURE 5

In FIG. 5 the lens 20 is shown in position in the posterior chamber. The diameter of the circular rim surfaces 23a and 24a is the same diameter as the diameter of the capsular bag and cannot therefore decenter. The inferior arms are fitted into the interior of the capsular bag for fixation. The vectors of weight of the lens make it want to remain centered. The inferior curve surface 23a of the lens may be manipulated to glide easily into the bag without a tendency to penetrate the posterior capsule. Thus the lens of FIGS. 3 nd 4 will fixate and center in most cases without any additional fixation.

An additional unique provision is present in the lens of FIGS. 3 and 4 enhancing the ability to fixate the upper limb of the lens to the iris. This is achieved by providing a radial slit 26 extending from surface 24a into the aperture 25. In utilizing the same, an iridectomy is made over the rim segment 24. A piece of the iris is pressed through the slit 26. This may be achieved utilizing a small caliber blunt instrument. Thus the iris is grasped by the lens in a clipping or clawlike action. This further prevents the lens from dislocating should capsular fixation not occur by reason of the contact to the inferior supporting surface 23a. In addition, fixation at slit 26 utilizes the pendulum effect further to enhance fixation.

In FIG. 5 the jagged margins 30, 31 and 32 represent the opening made into the capsule for fragmentation and removal of the lens. The opening is adequate to receive the inferior rim segment 23 and to accommodate the insertion of the ends of the rim segment 24. The inner surface of the posterior capsule 33 may be viewed through the opening. The surface of the anterior capsule 34 only in part remains intact.

Typically the posterior chamber lens of FIGS. 3-5 would have the lens portion 20 of 4 to 6 millimeters in diameter with the rim segment 24 of about the same chord length and with rim 23 about twice such chord length and with the diameter of the outer surfaces 23a and 24a from the center of the lens 20 being of the order of 11.5 millimeters.

It will be understood that FIGS. 1 and 3 have been illustrated with the lenses oriented as would be viewed by the physician during an implant procedure. FIG. 5 on the other hand is a view of the lens area with the iris removed in order to permit the interior limbs to be shown as they are positioned within the capsular bag. In FIG. 5 the lens is in the position as to be viewed by an observer facing the patient with the implant.

The lens, limbs and rims may all be made of rigid material suitable for eye implant. Such material may be of the nature of polymethylmethacrylate (PMMA). In accordance with the principles described in Applicant's co-pending application Ser. No. 28,609, filed Apr. 9, 1979, the unit used for anterior chamber implantation may be made up of different materials for facilitating the accommodation of a lens through muscular action in the eye. For example, the lens itself and the rims may be of rigid material, such as polymethylmethacrylate (PMMA), while the limbs may be of a softer material of the nature of hydrogels (PHEMA).

Thus from the foregoing it will be seen that an intraocular implant lens is provided comprising a central circular lens with a narrow 12 o'clock limb and a narrow arcuate rim segment centered on the end of the 12 o'clock limb and extending about 15° along with a narrow six o'clock limb supporting a rim segment of about 30° arcuate extent. The arcuate segments have their center at the center of the lens and are of diameter of the chamber in which they are to be fixed.

I claim:

1. An intraocular implant unit for permanent installation and immobilization in a circularly bounded chamber in the eye of a patient comprising:
   (a) a lens;
   (b) a first limb and a second limb integral with and extending outward radially from opposite margins of said lens;
   (c) a long arcuate rim mounted at its center on the end of said first limb; and
   (d) a short arcuate rim defining an arcuate length of less extent than said long arcuate rim and being mounted at its center on the end of said second limb, wherein said rims conform to a circle having a diameter equal to the diameter of the circularly bounded chamber and wherein said rims have the same center of curvature.

2. The combination of claim 1 wherein said lens and said rims are substantially coplanar for capsular sac implantation.

3. The combination of claim 1 wherein the plane of said rims is posterior to said lens for anterior chamber implantation.

4. The combination of claim 1 wherein said rims and said limbs are substantially less in lateral dimension than the diameter of said lens for minimizing the weight of the implant unit.

5. The combination of claim 1 in which said lens is of the same material as said limbs and rims.

6. The combination of claim 1 where said lens and said rims are made of rigid material of the nature of polymethlmethacrylate (PMMA) and said limbs are of a softer material of the nature of hydrogels (PHEMA).

7. An intraocular implant unit comprising:
   (a) a lens;
   (b) a first limb and a second limb integral with and extending outward radially from opposite margins of said lens;
   (c) a long arcuate rim centered on the end of said first limb;
   (d) a short arcuate rim defining an arcuate length of less extent than said long arcuate rim and being centered on said second limb, wherein a radial slit extends toward said lens from the outer periphery of said short rim centered with reference to said second limb for clamping said short rim to tissue of a receptor.

8. The combination of claim 7 in which said slit terminates in a hole centered on said short rim and on said second limb.

9. An intraocular implant lens unit comprising:
   (a) a central lens;
   (b) a first limb and a second limb integral with and extending outward radially from opposite margins of said lens;

(c) a long arcuate rim conforming to a circle throughout its length and mounted at its center on the end of said first limb; and (d) a short arcuate rim defining an arcuate length of less extent than said long arcuate rim and forming part of a circle throughout its length and mounted at its center on the end of said second limb, said rims being curved and mounted to have a common center located at the center of said lens and of the same diameter as the diameter of the scleral spur.

10. An intraocular implant unit comprising:

(a) a central plano-convex lens;

(b) a narrow 12 o'clock limb and a narrow 6 o'clock limb integral with and extending outward radially from opposite margins of said lens;

(c) a narrow arcuate rim mounted at its center on the end of said 12 o'clock limb circumscribing a circular arc of about 15° extent; and (d) a narrow arcuate rim mounted at its center on the end of said 6 o'clock limb circumscribing a circular arc of about 30° extent, said rims having a common center located at about the center of said lens and of the same diameter as the diameter of the scleral spur.

11. An intraocular implant unit comprising:

(a) a lens;

(b) a first limb and a second limb integral with and extending outward radially from diametrically opposed marginal locations on said lens;

(c) a first arcuate rim segment centered on the end of said first limb having as its center of curvature the center of said lens; and (d) a second arcuate rim segment defining an arcuate length of less extent than said first arcuate rim segment and being centered on said second limb and having as its center of curvature the center of said lens, said arcuate rim segments having rounded smooth continuous outer edges for distribution of contact forces to the margin of a chamber of a host eye over the entire lengths of said rim segments.

12. The combination of claim 11 in which said lens has anterior and posterior surfaces and in which said rim segments lie in a support plane which is parallel to the principal plane of said lens but located posteriorly of said lens.

* * * * *

UNITED STATES PATENT AND TRADEMARK OFFICE
CERTIFICATE OF CORRECTION

PATENT NO. : 4,254,510

DATED : March 10, 1981

INVENTOR(S) : Jerald L. Tennant

It is certified that error appears in the above-identified patent and that said Letters Patent are hereby corrected as shown below:

Column 4, line 9, change "15°" to --30°--;
line 11, change "30°" to --60°--.
Column 5, line 20, change "15°" to --30°--;
line 23, change "30°" to --60°--.

Signed and Sealed this

Twenty-third Day of June 1981

[SEAL]

Attest:

RENE D. TEGTMEYER

Attesting Officer

Acting Commissioner of Patents and Trademarks